United States Patent
Imagawa

(10) Patent No.: US 9,958,388 B2
(45) Date of Patent: May 1, 2018

(54) IMAGING APPARATUS AND IMAGING METHOD

(71) Applicant: Panasonic Intellectual Property Management Co., Ltd., Osaka (JP)

(72) Inventor: Taro Imagawa, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days. days.

(21) Appl. No.: 15/810,804

(22) Filed: Nov. 13, 2017

(65) Prior Publication Data

US 2018/0067046 A1 Mar. 8, 2018

Related U.S. Application Data

(63) Continuation of application No. PCT/JP2016/003641, filed on Aug. 8, 2016.

(30) Foreign Application Priority Data

Aug. 28, 2015 (JP) .................................. 2015-168578

(51) Int. Cl.
*G01N 21/64* (2006.01)

(52) U.S. Cl.
CPC ....... *G01N 21/64* (2013.01); *G01N 2201/061* (2013.01)

(58) Field of Classification Search
CPC .... G01N 21/6456; G01N 21/64; G01N 21/55; G01N 2201/061
See application file for complete search history.

(56) References Cited

U.S. PATENT DOCUMENTS

| 7,330,749 B1 * | 2/2008 | Bhunachet | A61B 1/042 600/109 |
| 7,846,091 B2 * | 12/2010 | Fulghum | A61B 1/00009 600/160 |
| 9,119,552 B2 * | 9/2015 | Baumann | A61B 1/06 |
| 2002/0195586 A1 * | 12/2002 | Auslander | C09D 11/328 252/301.16 |

(Continued)

FOREIGN PATENT DOCUMENTS

| JP | 2011-092705 | 5/2011 |
| JP | 2014-035409 | 2/2014 |
| JP | 2015-087171 | 5/2015 |

OTHER PUBLICATIONS

International Search Report of PCT application No. PCT/JP2016/003641 dated Oct. 18, 2016.

*Primary Examiner* — Marcus Taningco
(74) *Attorney, Agent, or Firm* — Wenderoth, Lind & Ponack, L.L.P.

(57) ABSTRACT

A lighting unit illuminates an object with at least one type of excitation light and illumination light. An imaging unit captures images with at least one type of fluorescent light generated by the object illuminated with the excitation light, and with reflected light caused when the object reflects the illumination light. A fluorescent light detector generates a delay time distribution image of fluorescent light from a fluorescent light image captured by the imaging unit. A distance measuring unit generates a range image from a reflected light image captured by the imaging unit.

19 Claims, 11 Drawing Sheets

(56) References Cited

U.S. PATENT DOCUMENTS

| | | | |
|---|---|---|---|
| 2003/0041774 A1* | 3/2003 | Auslander | C09D 11/50 |
| | | | 106/31.32 |
| 2009/0131800 A1* | 5/2009 | Liang | A61B 5/0059 |
| | | | 600/476 |
| 2011/0085715 A1 | 4/2011 | Yan et al. | |
| 2011/0270092 A1* | 11/2011 | Kang | A61B 5/0071 |
| | | | 600/476 |
| 2012/0010465 A1* | 1/2012 | Erikawa | A61B 1/05 |
| | | | 600/109 |
| 2014/0086567 A1* | 3/2014 | Feke | G01N 21/6456 |
| | | | 396/4 |
| 2015/0185592 A1* | 7/2015 | Eineren | G03B 17/02 |
| | | | 348/375 |
| 2015/0198795 A1 | 7/2015 | Yamauchi et al. | |
| 2017/0276543 A1* | 9/2017 | Bogaki | G01J 1/0437 |

\* cited by examiner

IMAGING APPARATUS AND IMAGING METHOD

BACKGROUND

1. Technical Field

The present disclosure relates to an imaging apparatus for capturing an image by illuminating an object with light.

2. Description of Related Art

Disclosed in Japanese Patent Unexamined Publication No. 2015-87171 is a fluorescent light imaging apparatus for capturing an image with fluorescent light generated by an object illuminated with excitation light. In Japanese Patent Unexamined Publication No. 2015-87171, a degree of modulation in a change in intensity of fluorescent light and a phase in each of pixels in a fluorescent light image are acquired, phase differences between a reference point and other pixels in the fluorescent light image are acquired, fluorescent light components in each of the pixels in the fluorescent light image are determined, and a relative distance from the reference point is acquired.

SUMMARY

An imaging apparatus according to the present disclosure includes a lighting unit and an image acquisition unit. The lighting unit illuminates an object with at least one type of excitation light and illumination light. The image acquisition unit captures images with at least one type of fluorescent light radiated by the object illuminated with the excitation light, and with reflected light caused when the object reflects the illumination light. The image acquisition unit further acquires a delay time distribution image of the at least one type of fluorescent light, which is generated based on a delay time from when the excitation light enters to when the fluorescent light is radiated.

In an imaging method according to the present disclosure, an object is illuminated with at least one type of excitation light and illumination light. Images are further captured with reflected light caused when the object reflects the illumination light, and with fluorescent light generated by the object illuminated with the excitation light. Based on a result of the captured images, a delay time distribution image of at least one type of fluorescent light is acquired.

The imaging apparatus according to the present disclosure is capable of acquiring a delay time distribution image of fluorescent light of an object from a position away from the object.

DETAILED DESCRIPTION

Exemplary embodiments will be described herein in detail with reference to the drawings appropriately. However, detailed descriptions more than necessary might be sometimes omitted. For example, in some cases, detailed description of already well-known items and repeated description with respect to substantially the same configuration will be omitted. These omissions are made to avoid unnecessary redundancy of the following description, and to facilitate the understanding of those skilled in the art.

Note that the attached drawings and the following description are provided for those skilled in the art to fully understand the present disclosure, and are not intended to limit the subject matter as described in the appended claims. In other words, the exemplary embodiments that will be described herein each illustrate a specific example preferable to the present disclosure. Numerical values, components, arrangement and connection of the components, steps, an order of the steps, etc. shown in the following exemplary embodiments are mere examples, and are not intended to limit the technology of the present disclosure. Among the components in the following exemplary embodiments, components not recited in any of independent claims indicating the most generic concept of the present disclosure are described as optional components configuring a preferable exemplary embodiment.

First Exemplary Embodiment

A first exemplary embodiment will now be described herein with reference to FIGS. 1 to 7.

[1-1. Configuration]

Figure 1:
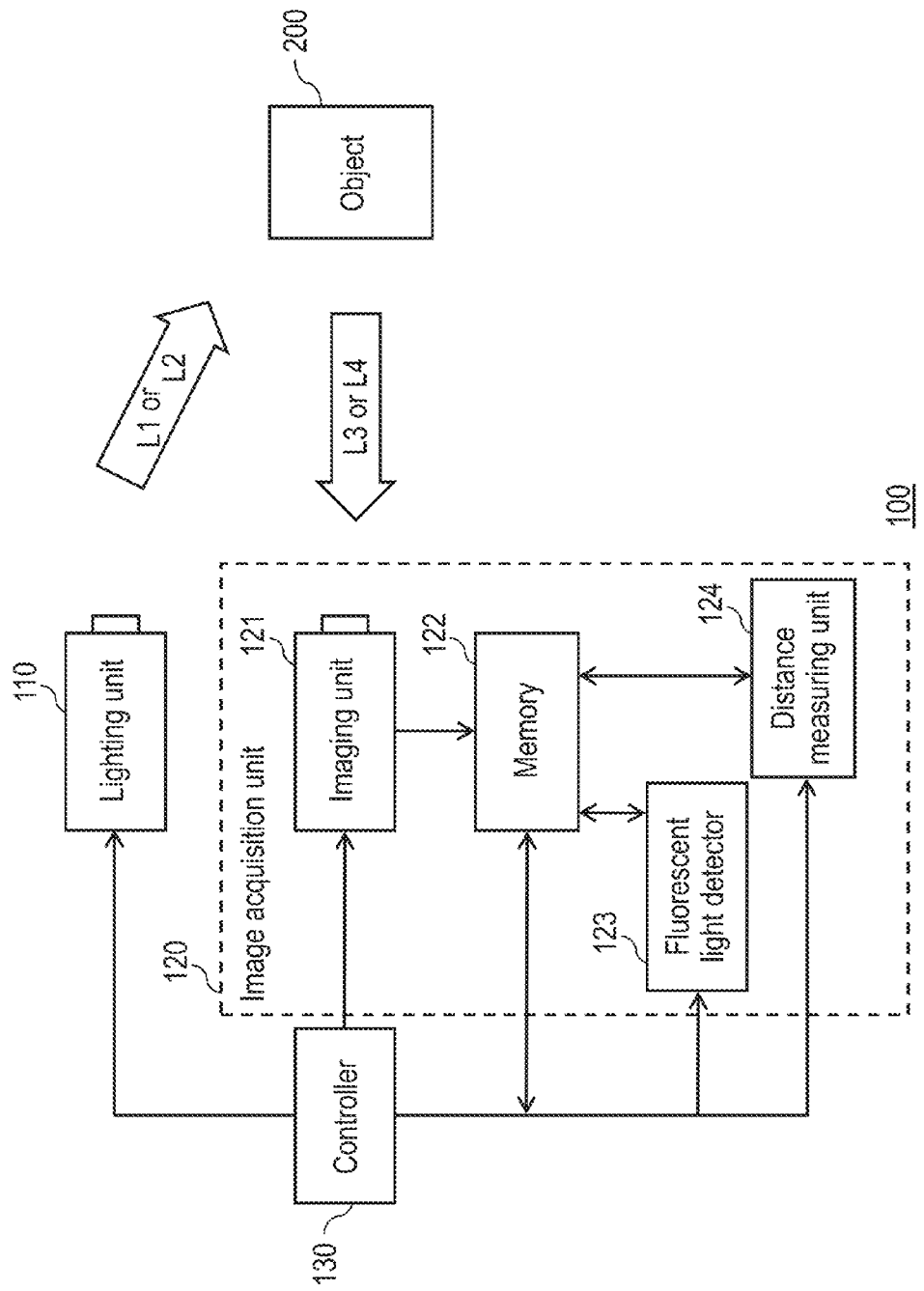
FIG. 1 is a schematic view illustrating a specific configuration of an imaging apparatus according to a first exemplary embodiment.

FIG. 1 is a schematic view illustrating a specific configuration of imaging apparatus 100 according to the first exemplary embodiment.

As shown in FIG. 1, imaging apparatus 100 according to the present disclosure includes lighting unit 110, image acquisition unit 120, and controller 130. Image acquisition unit 120 includes imaging unit 121, memory 122, fluorescent light detector 123, and distance measuring unit 124.

Lighting unit 110 exclusively illuminates object 200 with at least one type of excitation light and illumination light. Lighting unit 110 includes, for example, a light emitting unit for emitting the illumination light, and another light emitting unit for emitting the at least one type of excitation light. Lighting unit 110 may be configured to follow control of controller 130 to cause either of the light emitting units to emit light. Lighting unit 110 may take any configuration as long as excitation light and illumination light are emitted in a switched manner.

Lighting unit 110 according to this exemplary embodiment emits one type of excitation light L1 and illumination light L2. Controller 130 selects light to be emitted per predetermined exposure time (period for capturing a one-frame image). Lighting unit 110 follows control of controller 130 to illuminate object 200 with the selected light at a predetermined illumination timing.

Illumination light in here refers to light illuminated to object 200 to observe reflected light reflected by object 200. Excitation light refers to light illuminated to object 200 to cause object 200 to generate fluorescent light. In other words, excitation light refers to light illuminated to object 200 to observe fluorescent light emitted from object 200. In the present disclosure, an image indicative of a delay time from when excitation light is illuminated to object 200 to when fluorescent light is emitted is referred to as a delay time distribution image of fluorescent light. A delay time distribution image of fluorescent light is an image having per pixel a value of a time of delay, which is caused when fluorescent light is generated, in a time of arrival to imaging apparatus 100.

In the present disclosure, ultra-violet light (short wavelength light) is used as excitation light L1. Excitation light L1 may be light other than ultra-violet light. Excitation light L1 may be light having a wavelength that falls around an upper limit of an imaging wavelength band for imaging unit 121, or light having a shorter wavelength than a wavelength that falls within the imaging wavelength band. Visible light may be used, for example. An imaging wavelength band refers to a range of wavelengths of light with which imaging unit 121 can capture an image.

In the present disclosure, near-infrared light (long wavelength light) is used as illumination light L2. Illumination light L2 may be light other than near-infrared light as long as the light has a wavelength that falls within the imaging wavelength band. Illumination light L2 may be light having a wavelength that falls around a lower limit of the imaging wavelength band for imaging unit 121.

Image acquisition unit 120 receives fluorescent light L3 or reflected light L4. Fluorescent light L3 is light radiated by object 200 illuminated with excitation light L1. Reflected light L4 is light caused when object 200 reflects illumination light L2 illuminated from lighting unit 110. Image acquisition unit 120 performs exposure at an exposure timing synchronized with an illumination timing in a predetermined exposure time. Image acquisition unit 120 acquires a delay time distribution image of fluorescent light and a range image based on fluorescent light L3 and reflected light L4 received in the predetermined exposure time. In the present disclosure, image acquisition unit 120 is described as a monochromatic camera (camera for capturing images with visible light and near-infrared light). Image acquisition unit 120 internally includes components such as an I/O port, a memory for storing a program, and a processor for executing the program.

Imaging unit 121 includes an optical system such as an image sensor and a lens. In this exemplary embodiment, imaging unit 121 includes a scanning CMOS image sensor. Imaging unit 121 captures an image with fluorescent light L3 or reflected light L4 having a wavelength that falls within the imaging wavelength band. Imaging unit 121 performs in plural times exposure operations at predetermined exposure timings in an exposure time to capture images. Imaging unit 121 stores the captured images in memory 122.

Memory 122 is, for example, a frame memory that is an image signal storage device configured to store image signals corresponding to a plurality of frames. A semiconductor storage element capable of operating at a higher speed, such as a DRAM, is used to configure memory 122. Memory 122 may be configured to lie in controller 130, i.e., outside of image acquisition unit 120.

Fluorescent light detector 123 calculates times of flight (TOF) for excitation light L1 and illumination light L2 based on images respectively captured by imaging unit 121 with fluorescent light L3 and reflected light L4. Fluorescent light detector 123 calculates a time of fluorescence delay based on the TOF for excitation light L1 and the TOF for illumination light L2. Fluorescent light detector 123 generates a delay time distribution image of fluorescent light based on the calculated time of fluorescence delay.

Distance measuring unit 124 estimates a distance from imaging unit 121 to object 200 based on a plurality of images captured with reflected light L4 using a Time Of Flight (TOF) method. Distance measuring unit 124 generates a range image of object 200 based on the estimated distance from imaging unit 121 to object 200. A range image is also referred to as a depth map. A plurality of images captured with reflected light L4 is images captured by imaging unit 121 in an exposure period and stored in memory 122.

Controller 130 includes, for example, a non-volatile memory in which a program is stored, a volatile memory representing a temporary storage area for executing the program, an I/O port, and a processor for executing the program. Controller 130 selects light to be illuminated by lighting unit 110, and controls a light illumination timing, an exposure timing for imaging unit 121, and an exposure time representing a length of an exposure period. Controller 130 also controls operation of fluorescent light detector 123 and distance measuring unit 124.

[1-2. Operation]

Figure 2:
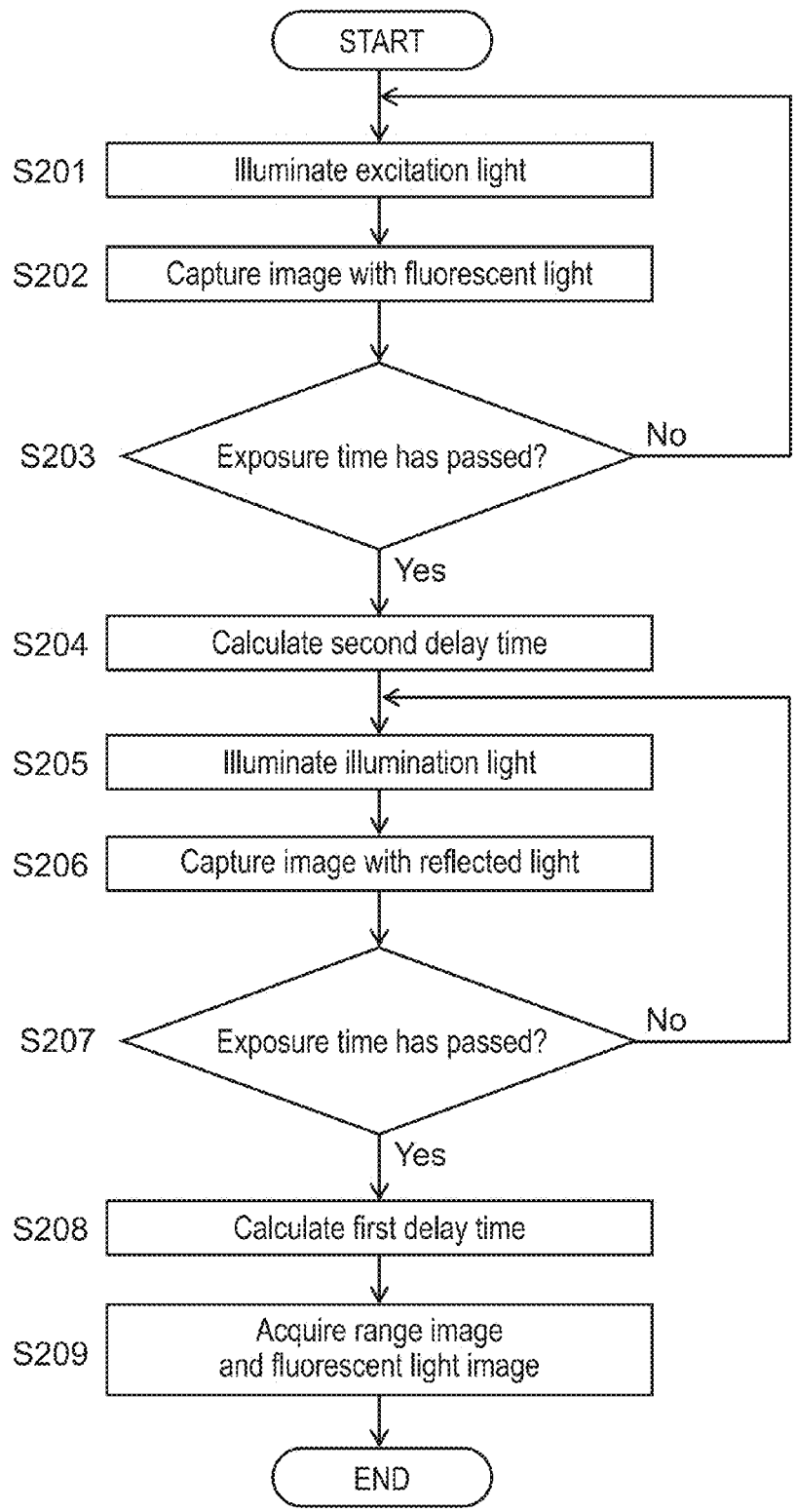
FIG. 2 is a flowchart for describing operation of the imaging apparatus according to the first exemplary embodiment.

Operation (an imaging method) of the imaging apparatus configured as described above will now be described herein with reference to FIG. 2. FIG. 2 is a flowchart for describing operation of imaging apparatus 100 according to the first exemplary embodiment.

(Step S201)

Controller 130 uses illumination timing signals to perform controlling so that lighting unit 110 illuminates object 200 with excitation light L1 at predetermined timings. Lighting unit 110 follows the illumination timing signals to illuminate object 200 with excitation light L1. In the present disclosure, lighting unit 110 uses ultra-violet light as excitation light L1.

(Step S202)

Controller 130 controls an exposure operation of imaging unit 121 using exposure timing signals synchronized with the illumination timing signals. Controller 130 outputs the exposure timing signals to imaging unit 121. Imaging unit 121 follows the exposure timing signals to perform the exposure operations. In the present disclosure, controller 130 outputs two types of exposure timing signals to imaging unit 121. In other words, imaging unit 121 performs two types of exposure in synchronization with the illumination timing signals for lighting unit 110 to capture images with fluorescent light L3.

Figure 3:
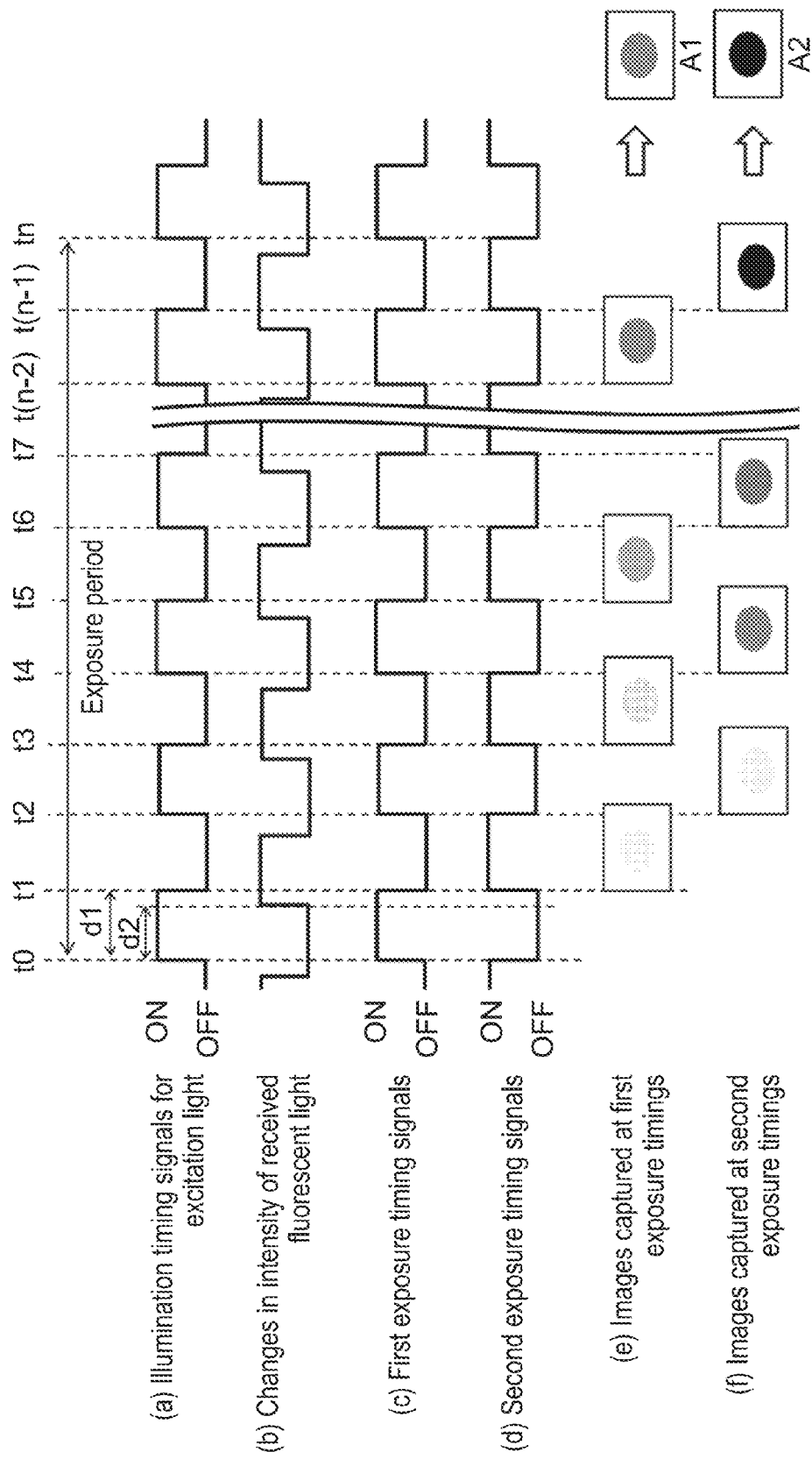
FIG. 3 is a view for describing operation when the imaging apparatus according to the first exemplary embodiment illuminates excitation light.

Operation when imaging apparatus 100 illuminates excitation light will now be described herein with reference to FIG. 3. FIG. 3 is a view for describing operation when imaging apparatus 100 according to the first exemplary embodiment illuminates excitation light.

FIG. 3 illustrates the operation of imaging apparatus 100 in an exposure period ranging from time t0 to time tn.

Illumination timing signals for excitation light shown in FIG. 3 represent illumination timing signals used for controlling timings at which lighting unit 110 illuminates excitation light. ON and OFF of the illumination timing signals for excitation light represent an illumination state and a non-illumination state, respectively. Changes in intensity of received fluorescent light shown in FIG. 3 represent, as for fluorescent light L3 radiated by object 200 illuminated with excitation light L1, time changes in intensity of fluorescent light L3 entering into imaging unit 121. FIG. 3 shows first exposure timing signals and second exposure timing signals for controlling two types of exposure timings for imaging unit 121. In FIG. 3, ON and OFF of the first exposure timing signals and the second exposure timing signals represent a light exposing state and a non-light exposing state of imaging unit 121, respectively. Images captured at first exposure timings shown in FIG. 3 are schematic views of images captured in accordance with the first exposure timing signals. Images captured at second exposure timings shown in FIG. 3 are schematic views of images captured in accordance with the second exposure timing signals.

As can be seen from the illumination timing signals for excitation light shown in FIG. 3, lighting unit 110 repeats operations of illumination and non-illumination of excitation light L1 per predetermined time d1 in the exposure period. As described above, in the present disclosure, excitation light is illuminated in plural times for once (one frame) capturing a delay time distribution image of fluorescent light and a range image.

As shown in FIG. 3, imaging unit 121 receives fluorescent light L3 generated by object 200 illuminated with excitation light L1. A timing when imaging unit 121 receives fluorescent light L3 delays, with respect to an illumination timing for lighting unit 110, by a time obtained by adding a TOF for light reaching object 200 (first delay time) and a time of occurrence of delayed fluorescent light generated by object 200 in response to excitation light L1 (time of fluorescence delay). In the example shown in FIG. 3, a light receiving timing delays by time d2 from an illumination timing. To detect second delay time (first delay time+time of fluorescence delay) d2, imaging unit 121 according to the present disclosure in here captures images of object 200 in response to two types of time-modulated exposure timing signals. Imaging unit 121 stores the captured images in succession in memory 122.

As shown in FIG. 3, the first and second exposure timing signals are in synchronization with the illumination timing signals for excitation light. The first exposure timing signals are signals each having a phase identical to a phase of each of the illumination timing signals. For example, imaging unit 121 performs an exposure operation in a period ranging from time t0 to time t1, during which lighting unit 110 illuminates light, while imaging unit 121 does not perform an exposure operation in a period ranging from time t1 to time t2, during which lighting unit 110 does not illuminate excitation light. On the other hand, the second exposure timing signals are signals each having a phase opposite to the phase of each of the illumination timing signals. For example, an exposure operation is not performed in a period ranging from time t0 to time t1, during which lighting unit 110 illuminates excitation light, while an exposure operation is performed in a period ranging from time t1 to time t2, during which lighting unit 110 does not illuminate light.

As shown in FIG. 3, in a period when exposure is performed in accordance with a first exposure timing signal, a period during which imaging unit 121 receives fluorescent light L3 corresponds to a period between an end of time d2 that has started when the exposure starts and an end of the exposure. Upon imaging unit 121 finishes exposure once, an image is stored in memory 122.

Similarly, as shown in FIG. 3, in exposure in accordance with a second exposure timing signal, imaging unit 121 receives fluorescent light L3 from when the exposure starts. Upon imaging unit 121 finishes exposure once, an image is stored in memory 122. In this case, in the exposure in accordance with the second exposure timing signal, fluorescent light L3, which has not yet been received in the exposure in accordance with the first exposure timing signal, is received for capturing an image. In other words, performing exposure twice can securely receive fluorescent light L3 generated in response to excitation light L1 that has been illuminated once.

For example, a first delay time might be shorter when object 200 lies near imaging apparatus 100, and thus an image can more likely be captured with fluorescent light L3 in exposure in accordance with a first exposure timing signal. On the other hand, a first delay time might be longer when object 200 lies away from imaging apparatus 100, and thus an image can more likely be captured with fluorescent light L3 in exposure in accordance with a second exposure timing signal. As described above, performing exposure twice in single illumination can allow fluorescent light L3 to be captured in an image in either or both of the exposure.

In the exposure period, imaging unit 121 acquires images captured at timings corresponding to the first exposure timings and images captured at timings corresponding to the second exposure timings respectively in number corresponding to a number of times of the exposure. Imaging unit 121 acquires image A1 from a plurality of the images captured at the first exposure timings. Imaging unit 121 also acquires image A2 from a plurality of the images captured at the second exposure timings.

As described above, in an exposure period, illumination of and exposure with excitation light are repeated in plural times. Fluorescent light L3 radiated by object 200 illuminated with excitation light generally has a lower intensity. Due to this lower intensity of fluorescent light L3, noise in an image captured with fluorescent light L3 can be problematic. Combining a plurality of images captured with fluorescent light L3 can however improve an SN ratio. An intensity of fluorescent light L3 to be received by imaging unit 121 can therefore be further precisely be estimated. All of a plurality of images captured at first exposure timings may not be stored in memory 122. For example, a newly captured image may be added to an image stored in memory 122 through an arithmetic operation. All of a plurality of images captured at second exposure timings may not be stored as well.

(Step S203)

After imaging unit 121 starts capturing of an image, controller 130 determines whether the exposure time has passed. Controller 130 calculates an image capturing time by using a timer or by counting a number of rectangles of exposure timing signals, for example. Upon controller 130 determines that the image capturing time has not yet reached the exposure time, controller 130 returns to step S201. Upon controller 130 determines that the image capturing time has reached the exposure time, controller 130 proceeds to step S204.

(Step S204)

Controller 130 calculates a second delay time per pixel in an image captured by imaging unit 121. A second delay time is taken into account in a range of one cycle of an illumination modulation. In FIG. 3, for example, one cycle of an illumination modulation refers to time d1 ranging from time t0 to time t1. Second delay time d2 shown in FIG. 3 is associated with a difference between an amount of exposure at a first exposure timing (amount of light received by imaging unit 121 while exposure is performed) and an amount of exposure at a second exposure timing, both of which are acquired in step S202, and respectively have phases different from each other. For example, when second delay time d2 is a half of time d1, a difference between an amount of exposure at a first exposure timing and an amount of exposure at a second exposure timing is 0. A ratio between the amount of exposure at the first exposure timing and the amount of exposure at the second exposure timing is at this time 1. As described above, a ratio between time d1 and second delay time d2 can be estimated from a ratio between an amount of exposure at a first exposure timing and an amount of exposure at a second exposure timing. By acquiring beforehand a relation between second delay time d2 and a difference or a ratio between an amount of exposure at a first exposure timing and an amount of exposure at a second exposure timing, and using a result of exposure, second delay time d2 can be acquired. When acquiring second delay time d2 based on a difference between an amount of exposure at a first exposure timing and an amount of exposure at a second exposure timing, a difference in amount of exposure also depends on a distance to an object. Therefore, a sum of an amount of exposure at a first exposure timing and an amount of exposure at a second exposure timing is used for normalization, or another measure is performed, and then an association with second delay time d2 is made.

(Step S205)

Controller 130 uses illumination timing signals for illumination light to perform controlling so that lighting unit 110 illuminates object 200 with illumination light L2 at predetermined timings. Lighting unit 110 follows the illumination timing signals for illumination light to illuminate object 200 with illumination light L2. In the present disclosure, lighting unit 110 uses near-infrared light as illumination light L2.

(Step S206)

Controller 130 controls an exposure operation of imaging unit 121 using exposure timing signals synchronized with the illumination timing signals. Controller 130 outputs the exposure timing signals to imaging unit 121. Imaging unit 121 follows the exposure timing signals to perform the exposure operations. In the present disclosure, controller 130 outputs two types of exposure timing signals to imaging unit 121. In other words, imaging unit 121 performs two types of exposure in synchronization with the illumination timing signals for lighting unit 110 to capture images with reflected light L4.

Figure 4:
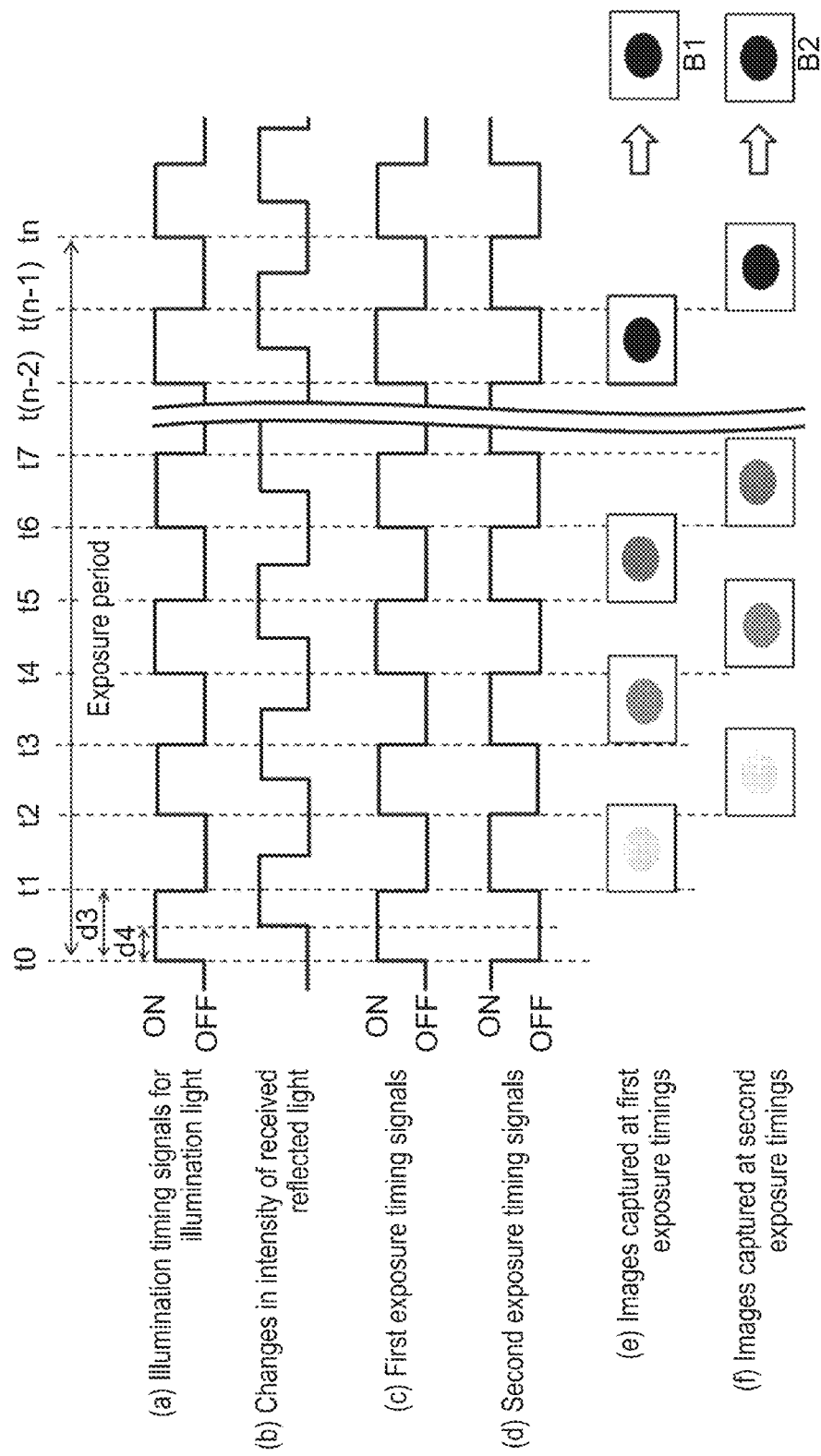
FIG. 4 is a view for describing operation when the imaging apparatus according to the first exemplary embodiment illuminates illumination light.

Operation when imaging apparatus 100 illuminates illumination light will now be described herein with reference to FIG. 4. FIG. 4 is a view for describing operation when imaging apparatus 100 according to the first exemplary embodiment illuminates illumination light. FIG. 4 illustrates the operation of imaging apparatus 100 in an exposure period ranging from time t0 to time tn.

Illumination timing signals for illumination light shown in FIG. 4 represent illumination timing signals used for controlling timings at which lighting unit 110 illuminates illumination light. ON and OFF of the illumination timing signals for illumination light represent an illumination state and a non-illumination state, respectively. Changes in intensity of received reflected light represent, as for reflected light L4 caused when object 200 reflects illumination light L2, time changes in intensity of reflected light L4 entering into imaging unit 121. FIG. 4 shows first exposure timing signals and second exposure timing signals for controlling two types of exposure timings for imaging unit 121. In FIG. 4, ON and OFF of the first exposure timing signals and the second exposure timing signals represent a light exposing state and non-light exposing state of imaging unit 121, respectively. Images captured at first exposure timings shown in FIG. 4 are schematic views of images captured in accordance with the first exposure timing signals. Images captured at second exposure timings shown in FIG. 4 are schematic views of images captured in accordance with the second exposure timing signals.

As can be seen from the illumination timing signals for illumination light as shown in FIG. 4, lighting unit 110 repeats operations of illumination and non-illumination per predetermined time d3 in the exposure period. As described above, in the present disclosure, illumination light is illuminated in plural times for once (one frame) capturing a range image. An exposure time when illuminating excitation light and an exposure time when illuminating illumination light may not be identical. Exposure times may differ between excitation light L1 and illumination light L2, since an illumination intensity and sensitivity of imaging unit 121 might differ. Similarly, when a plurality of types of excitation light is used, an exposure time may be changed per excitation light.

As shown in FIG. 4, imaging unit 121 receives reflected light L4 caused when object 200 reflects illumination light L2. A timing when imaging unit 121 receives reflected light L4 delays, with respect to an illumination timing for lighting unit 110, by a TOF for light reaching object 200 (first delay time). In the example shown in FIG. 4, a light receiving timing delays by time d4 from an illumination timing. To detect first delay time d4, imaging unit 121 according to the present disclosure in here captures images of object 200 in response to two types of time-modulated exposure timing signals. Imaging unit 121 stores the captured images in succession in memory 122.

As shown in FIG. 4, the first and second exposure timing signals are in synchronization with the illumination timing signals for illumination light. The first exposure timing signals are signals each having a phase identical to a phase of each of the illumination timing signals. On the other hand, the second exposure timing signals are signals each having a phase opposite to the phase of each of the illumination timing signals. The first and second exposure timing signals are identical to the first and second exposure timing signals shown in FIG. 3, and thus will not be described.

As shown in FIG. 4, in a period when exposure is performed in accordance with a first exposure timing signal, a period during which imaging unit 121 receives reflected light L4 corresponds to a period between an end of time d4 that has started when the exposure starts and an end of the exposure. Upon imaging unit 121 finishes exposure once, an image is stored in memory 122.

Similarly, as shown in FIG. 4, in exposure in accordance with a second exposure timing signal, imaging unit 121 receives reflected light L4 from when the exposure starts. Upon imaging unit 121 finishes exposure once, an image is stored in memory 122. In the exposure in accordance with the second exposure timing signal, an image is captured with reflected light L4 received at a timing opposite to the timing of the exposure in accordance with the first exposure timing signal. In other words, performing exposure twice can securely receive reflected light L4 caused when illumination light L2 illuminated once is reflected. When illumination light L2 is illuminated, similar to when excitation light L1 is illuminated, a positional relation between imaging apparatus 100 and object 200 allows capturing of an image with reflected light L4 through either or both of exposure in accordance with a first exposure timing signal and exposure in accordance with a second exposure timing signal.

In the exposure period, imaging unit 121 acquires images captured at timings corresponding to the first exposure timings and images captured at timings corresponding to the second exposure timings respectively in number corresponding to a number of times of the exposure. Imaging unit 121 acquires image B1 from a plurality of the images captured at the first exposure timings. Imaging unit 121 also acquires image B2 from a plurality of the images captured at the second exposure timings. A normal captured image can be generated using image B1 and image B2.

As described above, in an exposure period, illumination of and exposure with illumination light are repeated in plural times. Performing illumination and exposure in plural times can improve an SN ratio in capturing images with reflected light L4, similar to when capturing images with fluorescent light L3. An intensity of reflected light L4 can therefore further precisely be estimated by imaging unit 121.

(Step S207)

After imaging unit 121 starts capturing of an image, controller 130 determines whether the exposure time has passed. Controller 130 calculates an image capturing time by using a timer or by counting a number of rectangles of exposure timing signals, for example. Upon controller 130 determines that the image capturing time has not yet reached the exposure time, controller 130 returns to step S205. Upon controller 130 determines that the image capturing time has reached the exposure time, controller 130 proceeds to step S208.

(Step S208)

With a procedure similar to a procedure of step S204, controller 130 calculates first delay time d4 per pixel in an image captured by imaging unit 121. Similar to step S204, by acquiring beforehand a relation between first delay time d4 and a difference or a ratio between an amount of exposure at a first exposure timing and an amount of exposure at a second exposure timing, and using a result of exposure, first delay time d4 may be acquired.

(Step S209)

Controller 130 acquires a range image and a delay time distribution image of fluorescent light of object 200 based on second delay time d2 acquired in step S204 and first delay time d4 acquired in step S208. Specifically, controller 130 controls distance measuring unit 124 to generate a range image based on first delay time d4. Distance measuring unit 124 calculates distance D (m) reaching object 200 per pixel to generate a range image. Distance D can be calculated with D=(d4/2)×light speed. Where, a light speed is specified to 299,792,458 (m/s).

Controller 130 also controls fluorescent light detector 123 to generate a delay time distribution image of fluorescent light based on first delay time d4 and second delay time d2, both of which have been calculated per pixel. Fluorescent light detector 123 calculates time of fluorescence delay τ per pixel to generate a delay time distribution image of fluorescent light. Time of fluorescence delay τ can be calculated with τ=d2−d4. The generated range image and the generated delay time distribution image of fluorescent light are stored in memory 122.

The operation of imaging apparatus 100 in one exposure period (one frame) has been described above. Operation from steps S201 to S209 may be repeated as required. By repeating the operation in plural times, range images and delay time distribution images of fluorescent light can be acquired as moving images.

Figure 5:
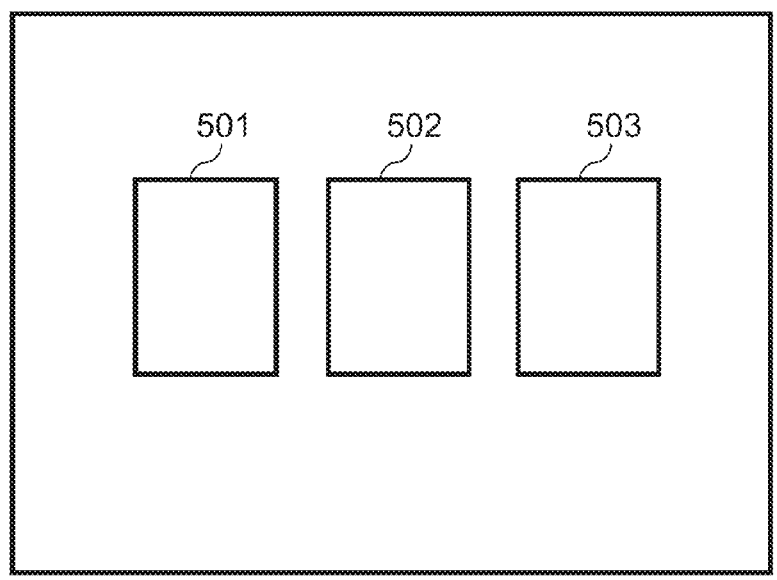
FIG. 5 is a view for describing an example of objects.
Figure 6:
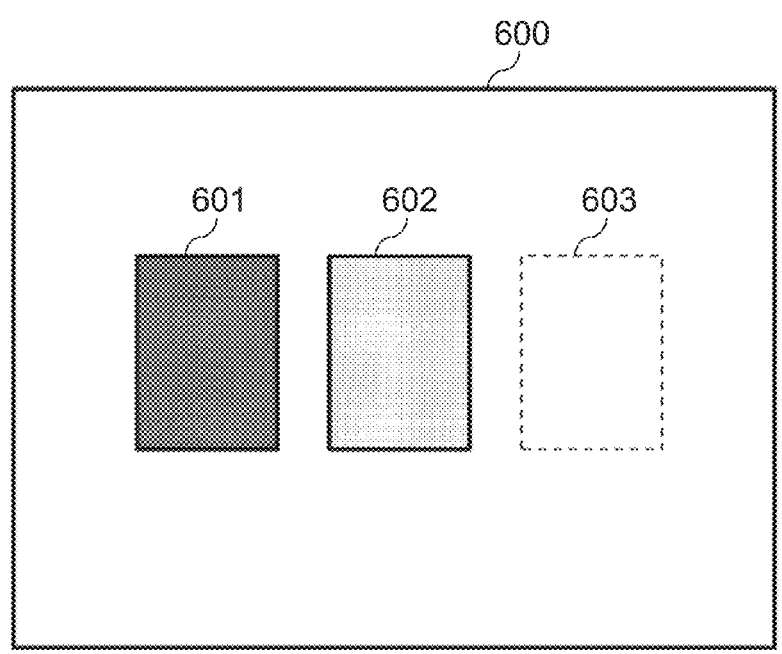
FIG. 6 is a view for describing an example of delay time distribution images of fluorescent light.
Figure 7:
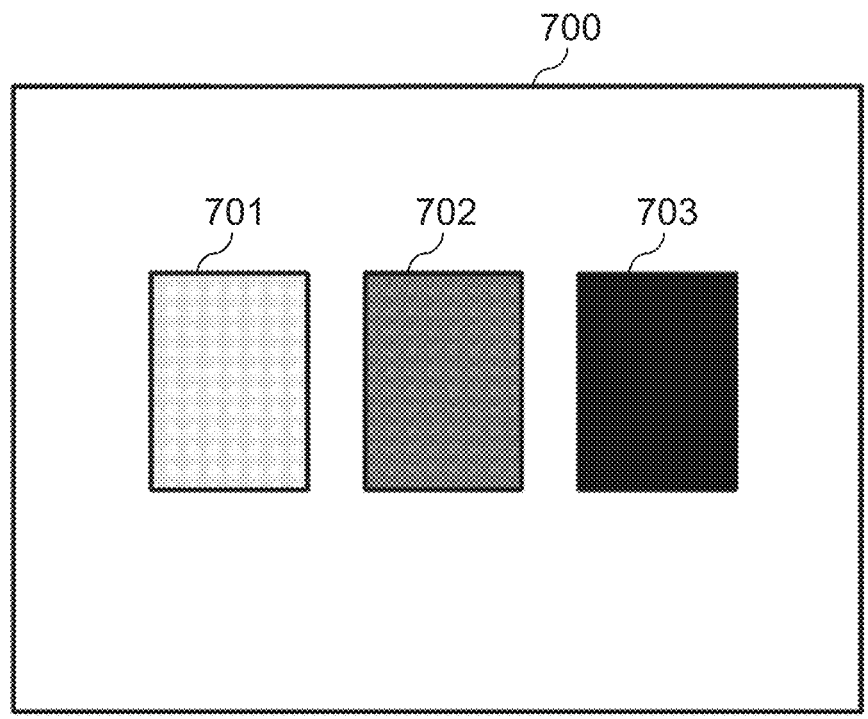
FIG. 7 is a view for describing an example of range images.

A specific example of this exemplary embodiment will now be described herein with reference to FIGS. 5 to 7. FIG. 5 is a view for describing an example of objects. FIG. 6 is a view for describing an example of delay time distribution images of fluorescent light. FIG. 7 is a view for describing an example of range images.

FIG. 5 is the example of the objects for which imaging apparatus 100 captures images. Three objects 501 to 503 are assumed to each have a different distance from imaging apparatus 100 and a different time of fluorescence delay.

FIG. 6 illustrates delay time distribution image of fluorescent light 600 formed by capturing and acquiring images of objects 501 to 503 with the imaging method according to the first exemplary embodiment. Rectangles 601 to 603 respectively are delay time distribution images of fluorescent light, which correspond to objects 501 to 503. In FIG. 6, rectangle 603 rendered with a dotted line indicates that object 503 has not generated fluorescent light with excitation light L1. Rectangles 601 and 602 indicate that objects 501 and 502 have generated fluorescent light, where object 501 shows a longer time of fluorescence delay.

FIG. 7 illustrates range image 700 formed by capturing and acquiring images of objects 501 to 503 with the imaging method according to the first exemplary embodiment. Rectangles 701 to 703 respectively are delay time distribution images of fluorescent light, which correspond to objects 501 to 503. FIG. 7 shows that object 501 lies farthest from imaging apparatus 100, while object 503 lies nearest to imaging apparatus 100.

As can be seen from FIGS. 6, 7, for example, object 503 lies nearest to imaging apparatus 100, but does not contain a fluorescent material that generate fluorescent light when illuminated with excitation light L1. Also indicated are a fact that object 501 lies farthest from imaging apparatus 100, but generates fluorescent light when illuminated with excitation light L1, and a time of fluorescence delay in object 501.

[1-3. Effects and Other Benefits]

As described above, in this exemplary embodiment, imaging apparatus 100 includes lighting unit 110 and image acquisition unit 120. Lighting unit 110 illuminates object 200 with at least one type of excitation light L1 and illumination light L2. Image acquisition unit 120 captures images with at least one type of fluorescent light L3 generated by object 200 illuminated with excitation light L1, and with reflected light L4 caused when object 200 reflects illumination light L2. Image acquisition unit 120 further acquires a delay time distribution image of the at least one type of fluorescent light, which is generated based on a delay time for fluorescent light L3 and a delay time for reflected light L4. Image acquisition unit 120 acquires a range image generated based on the delay time for reflected light L4.

TOF d2 for excitation light L1 and TOF d4 for illumination light L2 with respect to object 200 can therefore be calculated.

A calculation process can thus be shared for a TOF for fluorescent light L3 corresponding to excitation light L1 and a TOF for reflected light L4 corresponding to illumination light L2. Time of fluorescence delay τ can also be measured promptly by illuminating two types of light each having a different wavelength. This apparatus can be achieved in a simple configuration, since no mechanical switching structure is required. Distance D from imaging apparatus 100 to object 200 can further be acquired based on the TOF for reflected light L4. A time of fluorescence delay is a characteristic specific to a substance, and can be used to measure a characteristic specific to a substance configuring an object from a distant position. Object 200 can thus easily be recognized with a delay time distribution image of fluorescent light.

Similarly, by configuring imaging unit 121 using a color camera, information on a fluorescence spectrum can also be acquired, in addition to a time of fluorescence delay. An image captured with a fluorescence spectrum can be generated with images A1, A2 shown in FIG. 3. In this case, recognizing a target and a state is also possible since a time of fluorescence delay and a fluorescence spectrum can both be acquired as characteristics specific to a substance configuring an object.

Second Exemplary Embodiment

A second exemplary embodiment will now be described herein with reference to FIGS. 8, 9.

[2-1. Configuration]

Imaging apparatus 100 according to the second exemplary embodiment is identical in specific configuration to the imaging apparatus according to the first exemplary embodiment, excluding its operation, which will now be described herein.

In imaging apparatus 100 according to the second exemplary embodiment, lighting unit 110 exclusively illuminates excitation light and illumination light in an exposure period. The second exemplary embodiment describes an example when one type of excitation light and illumination light are used. Controller 130 according to the second exemplary embodiment uses two types of illumination timing signals and four types of exposure timing signals to control lighting unit 110 and imaging unit 121.

Figure 8:
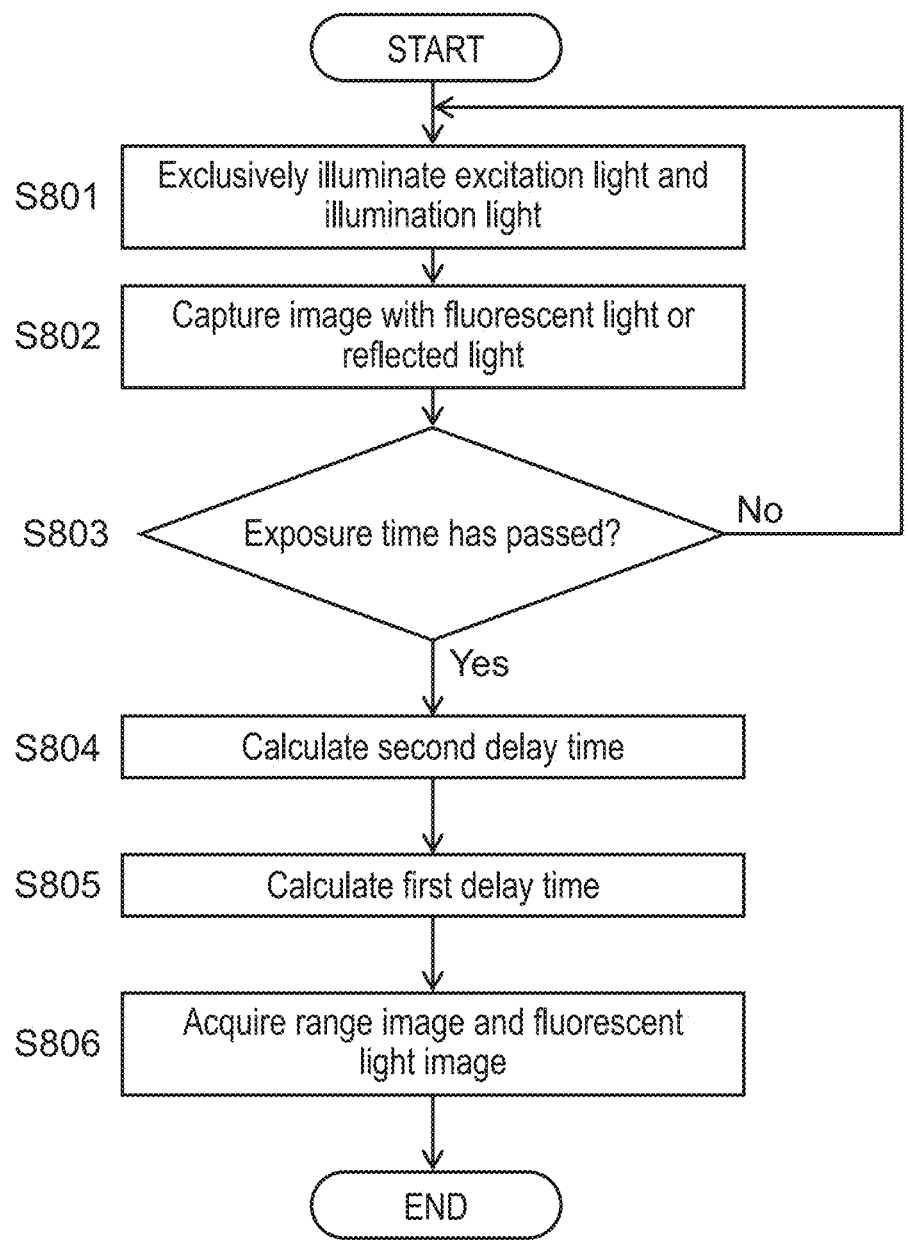
FIG. 8 is a flowchart for describing operation of an imaging apparatus according to a second exemplary embodiment.

FIG. 8 is a flowchart for describing operation (an imaging method) of imaging apparatus 100 according to the second exemplary embodiment. FIG. 9 is a view for describing the operation of imaging apparatus 100 according to the second exemplary embodiment.

Figure 9:
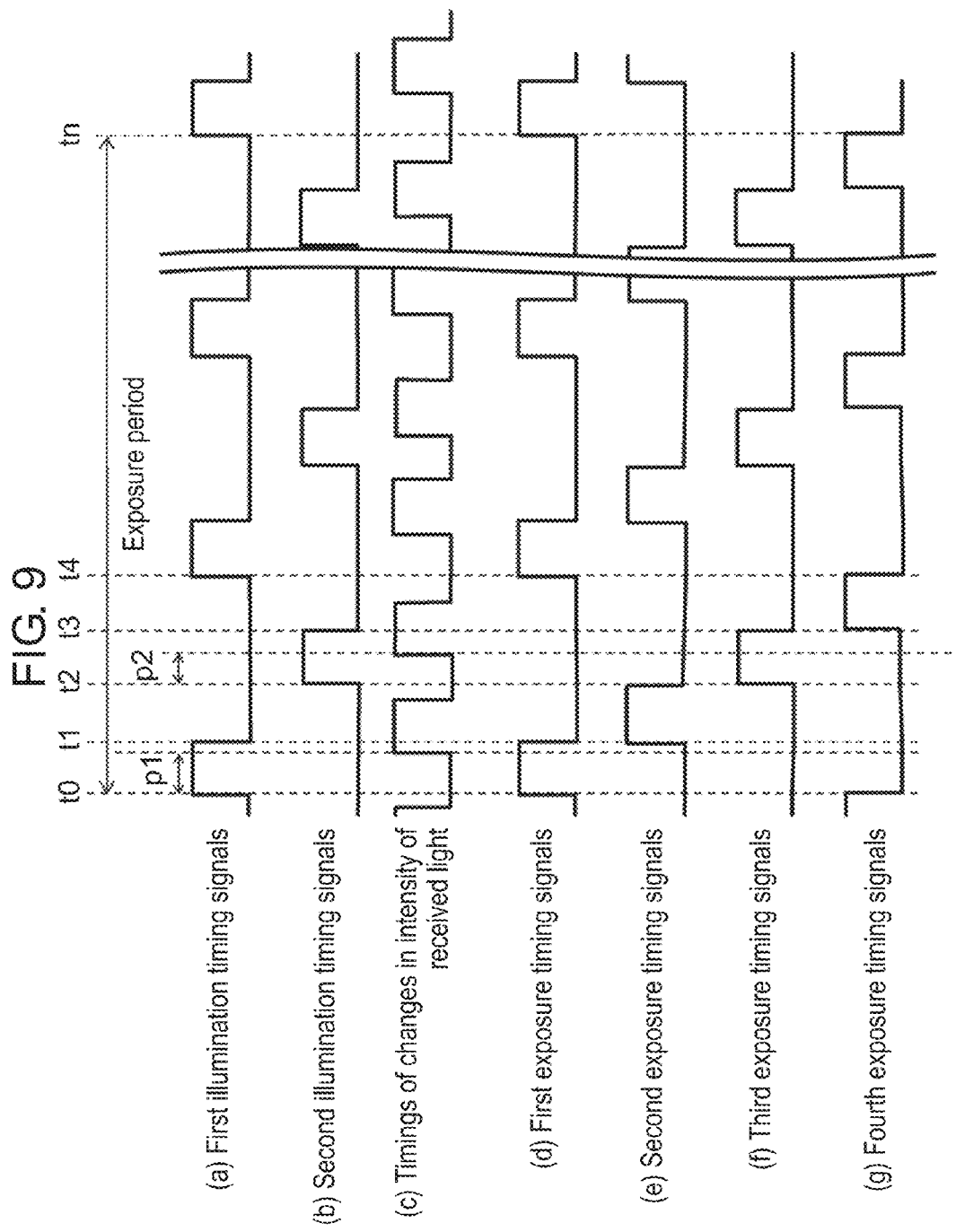
FIG. 9 is a view for describing the operation of the imaging apparatus according to the second exemplary embodiment.

FIG. 9 illustrates an example of timing signals for controlling lighting unit 110 and imaging unit 121 in an exposure time. FIG. 9 shows first illumination timing signals, second illumination timing signals, timings of changes in intensity of light received by imaging unit 121, first exposure timing signals, second exposure timing signals, third exposure timing signals, and fourth exposure timing signals. The timings of changes in intensity of received light represent timings at which intensities of fluorescent light L3 and reflected light L4 entering into imaging unit 121 change. An intensity and a waveform of light actually entering into imaging unit 121 differ between fluorescent light L3 and reflected light L4. FIG. 9 is however schematically illustrated by focusing on timings at which an intensity of light changes.

[2-2. Operation]

(Step S801)

Controller 130 uses illumination timing signals to control lighting unit 110. Lighting unit 110 exclusively illuminates object 200 with excitation light L1 and illumination light L2 in an exposure period based on the illumination timing signals. In the second exemplary embodiment, controller 130 uses two types of illumination timing signals to control one type of excitation light and illumination light. Lighting unit 110 alternately illuminates excitation light L1 and illumination light L2 in the exposure period based on the two types of illumination timing signals. As shown in FIG. 9, lighting unit 110 follows a first illumination timing signal to illuminate object 200 with excitation light L1 in a period ranging from time t0 to time t1. Next, lighting unit 110 follows a second illumination timing signal to illuminate object 200 with illumination light L2 in a period ranging from time t2 to time t3. Next, lighting unit 110 follows another first illumination timing signal to illuminate object 200 with excitation light L1 from time t4. As described above, lighting unit 110 follows two types of illumination timing signals to alternately illuminate excitation light L1 and illumination light L2.

(Step S802)

Controller 130 uses four types of exposure timing signals to control an exposure operation of imaging unit 121. As shown in FIG. 9, imaging apparatus 100 alternately receives fluorescent light L3 and reflected light L4 from object 200.

Imaging unit 121 follows two types of exposure timing signals each synchronized with the illumination timing signals and each having a different phase to perform four types of exposure per illumination timing signal. This is due to a difference between a delay of fluorescent light L3 corresponding to excitation light L1 and a delay of reflected light L4 corresponding to illumination light L2.

At first and second exposure timing signals, images are captured with fluorescent light L3 corresponding to excitation light L1 illuminated under the first illumination timing signals. This operation is similar to operation of step S202 in the first exemplary embodiment.

At third and fourth exposure timing signals, images are captured with reflected light L4 caused when illumination light L2 illuminated under the second illumination timing signal is reflected. This operation is similar to operation of S206 in the first exemplary embodiment.

(Step S803)

After imaging unit 121 starts capturing of an image, controller 130 determines whether the exposure time has passed. Controller 130 calculates an image capturing time by using a timer or by counting a number of rectangles of exposure timing signals, for example. Upon controller 130 determines that the image capturing time has reached the exposure time, controller 130 proceeds to step S804, while, upon controller 130 determines that the image capturing time has not yet reached the exposure time, controller 130 returns to step S801.

(Step S804)

Controller 130 calculates, per pixel, second delay time p1 for fluorescent light L3. Second delay time p1 is taken into account in a range of one cycle of an illumination modulation (in here, a time ranging from time t0 to time t1). Second delay time p1 is estimated based on an amount of exposure at a first exposure timing and an amount of exposure at a second exposure timing. For example, by acquiring beforehand a relation between second delay time p1 and a difference or a ratio between a first amount of exposure and a second amount of exposure, second delay time p1 may be acquired based on a result of exposure.

(Step S805)

Controller 130 calculates, per pixel, first delay time p2 for reflected light L4. First delay time p2 is taken into account in a range of one cycle of an illumination modulation (in here, a time ranging from time t2 to time t3). First delay time p2 is estimated based on an amount of exposure at a third exposure timing and an amount of exposure at a fourth exposure timing. For example, by acquiring beforehand a relation between first delay time p2 and a difference or a ratio between a third amount of exposure and a fourth amount of exposure, first delay time p2 is acquired based on a result of exposure.

(Step S806)

With a procedure similar to step S209, controller 130 uses fluorescent light detector 123 and distance measuring unit 124 to generate a range image and a delay time distribution image of fluorescent light. Fluorescent light detector 123 uses first delay time p2 and second delay time p1 to generate a delay time distribution image of fluorescent light. Distance measuring unit 124 uses first delay time p2 to generate a range image. The generated range image and the generated delay time distribution image of fluorescent light are stored in memory 122.

A step to finish a process for one exposure period (one frame) has been described. By repeating steps S801 to S806 as required, range images and delay time distribution images of fluorescent light can be acquired as moving images.

[2-3. Effects and Other Benefits]

As described above, in imaging apparatus 100 according to this second exemplary embodiment, lighting unit 110 exclusively illuminates excitation light L1 and illumination light L2 in a predetermined exposure time. Image acquisition unit 120 captures images with fluorescent light L3 and reflected light L4 each at two types of exposure timings.

TOF d2 and TOF d4 respectively for excitation light L1 and illumination light L2 with which object 200 is illuminated can therefore be calculated in a single exposure time.

A delay time distribution image of fluorescent light and a range image can therefore be acquired at an identical timing. When object 200 is moving, in particular, time changes can occur in magnitude of fluorescent light L3 and reflected light L4 in each pixel, and thus errors might increase in acquiring images with fluorescent light L3 and reflected light L4 respectively at different timings. This tendency is significant in fluorescent light L3 that will be affected by a difference in delay time between fluorescent light L3 and reflected light L4. Imaging apparatus 100 according to the second exemplary embodiment captures images with fluorescent light L3 and reflected light L4 at an almost identical timing. Acquiring a delay time distribution image of fluorescent light and a range image based on images captured with fluorescent light L3 and reflected light L4 at an almost identical timing can reduce effects caused by factors including when object 200 is moving.

Other Exemplary Embodiments

As above, the first and second exemplary embodiments have been described as illustration of the technology disclosed in the present application. However, the technology in the present disclosure is not limited to the first and second exemplary embodiments, and can also be applied to embodiments in which change, substitution, addition, omission and the like are performed. A new exemplary embodiment can also be made by a combination of the components of the first and second exemplary embodiments.

Accordingly, another exemplary embodiment will be described below.

In the present disclosure, timings at when a first exposure timing signal and a second exposure timing signal reach ON may at least differ. A first exposure timing signal and a second exposure timing signal may be signals each having a phase identical or opposite to a phase of an illumination timing signal. For example, an exposure timing signal may have a phase opposite to a phase of an illumination timing signal, while another exposure timing signal may have a phase that differs by a ¼ cycle, for example, from the phase of the illumination timing signal. A similar procedure described below can be achieved with a combination of exposure timing signals that are in synchronization with an illumination timing signal, but each have a shorter cycle. For example, a length of a cycle may be extended twice, and four types of exposure timing signals may be used to perform an exposure operation. This can also be applied to a relation between a third exposure timing signal and a fourth exposure timing signal in the second exemplary embodiment. In capturing images described above, capturing images with using an ultra-violet cut filter (optical filter) as required for reducing an effect of reflected light due to an illumination is advantageous.

Figure 10:
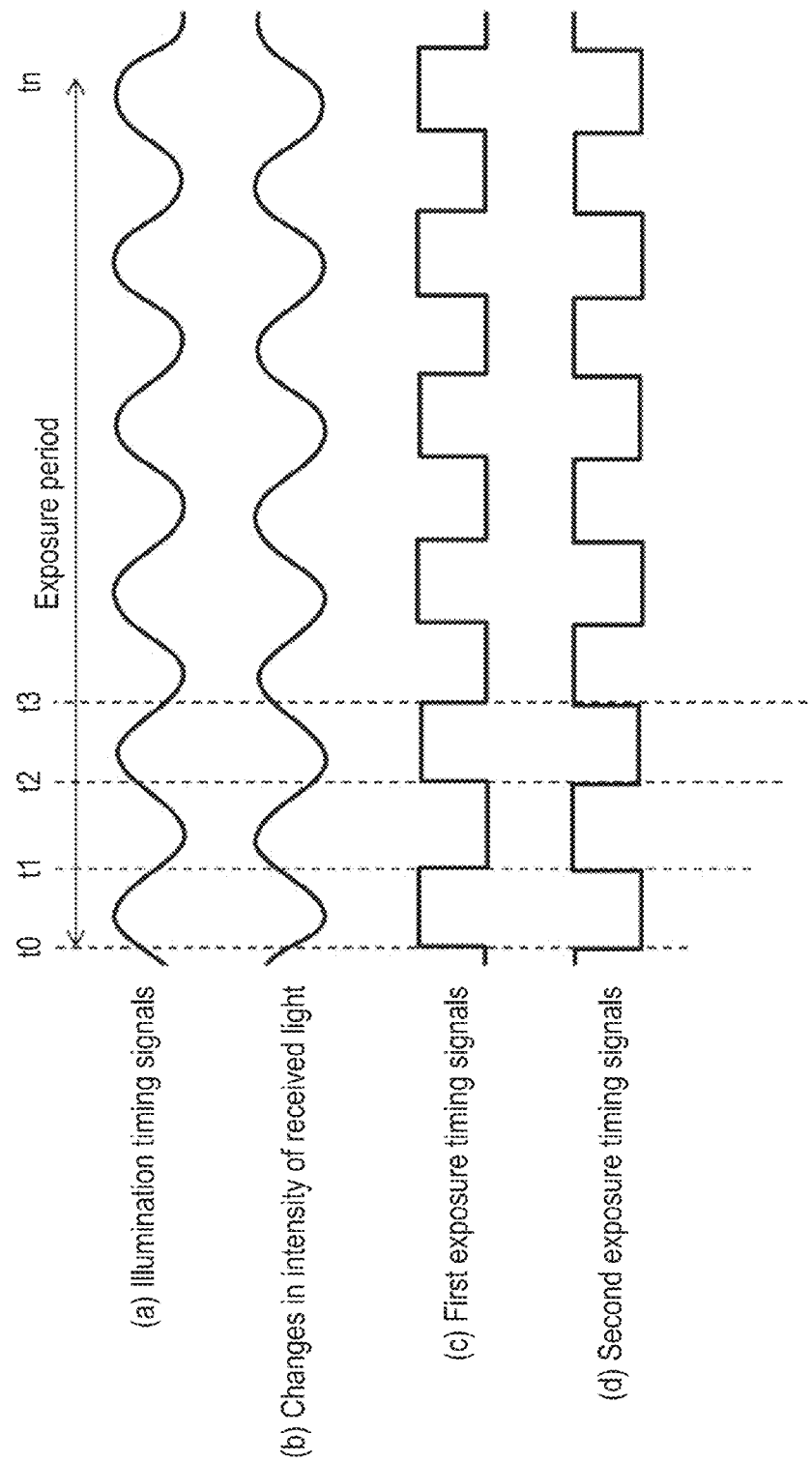
FIG. 10 is a view for describing another example of illumination timing signals.

In the present disclosure, rectangles have been used to describe changes in illumination intensity of lighting unit 110. However, other modulated waveforms can be used to achieve similar or identical effects. FIG. 10 is a view for describing another example of illumination timing signals. For an illumination timing signal, for example, a waveform of an illumination intensity may have a shape of a trigonometric function, as shown in FIG. 10. FIG. 10 shows illumination timing signals, timings of changes in intensity of received light, first exposure timing signals, and second exposure timing signals. The illumination timing signals represent signals used for controlling timings at which lighting unit 110 illuminates illumination light L2. The timings of changes in intensity of received light show time changes in intensity of reflected light L4 to be received by imaging unit 121. Reflected light L4 represents reflected light caused when lighting unit 110 illuminates object 200 with illumination light L2. In FIG. 10, a height of each of the illumination timing signals represents an intensity of illumination light L2. In the first exposure timing signals and the second exposure timing signals shown in FIG. 10, upper sides of rectangles each represent a light exposing state, while lower sides each represent a non-light exposing state.

In the present disclosure, a first delay time for reflected light and a second delay time for fluorescent light have been acquired in association with a difference or a ratio between two types of exposure timing signals each having a different time phase. However, another method may be used to acquire a delay time.

Figure 11:
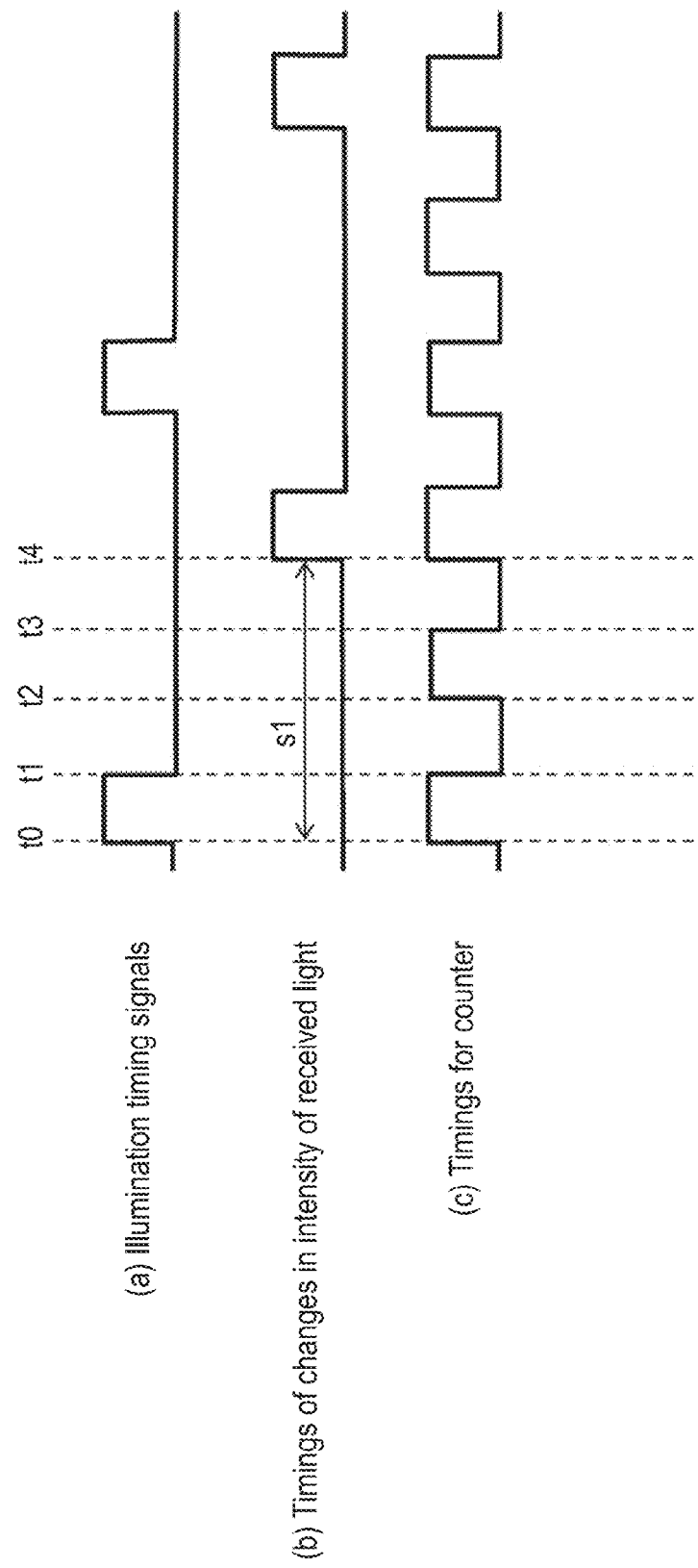
FIG. 11 is a view for describing another example of calculating a delay time.

Another method for acquiring a delay time will now be described herein with reference to FIG. 11. FIG. 11 illustrates illumination timing signals, timings of changes in intensity of received light, and timings for counter. The illumination timing signals represent timings at which lighting unit 110 illuminates illumination light L2 and excitation light L1. The timings of changes in intensity of received light schematically represent timings when an intensity of reflected light L4 or fluorescent light L3 received by imaging unit 121 changes. The timings for counter represent timings when counter signals for counting a delay time change. A cycle of counting counter signals is set in here fully shorter than an emission cycle and a delay time. Imaging unit 121 performs exposure when a counter signal is in an ON state only, in an OFF state only, or in both the ON and OFF states. In measuring a delay time, a number of counts counted until an amount of exposure exceeds a predetermined amount is determined as the delay time. The example in FIG. 11 assumes that an amount of received light is measured from time t0, and the amount of received light exceeds a predetermined amount at time t4. In this case, a delay time is determined to time s1 corresponding to two cycles of the counter. After a delay time has been determined for each of illumination, a fluorescent light image and a range image can be acquired, similar to the procedures in the first and second exemplary embodiments. A circuit capable of measuring a time may be used as a replacement to a counter method.

In the present disclosure, one type of excitation light has been used for description. However, two types or more of excitation light (short wavelength illumination) may be used in a switched manner. In this case, a different illumination timing signal may be used in accordance with a type of excitation light. An operation similar to the operation when one type of excitation light is used is performed per excitation light to acquire a delay time distribution image of fluorescent light. When a plurality of fluorescent materials is present in an object, use of a plurality of different types of illuminations can therefore be likely to highly effectively emit fluorescent light using one of the illuminations.

In the first exemplary embodiment, excitation light and illumination light are illuminated at different timings. However, excitation light and illumination light may be illuminated at an identical timing (even with opposite phases). In this case, in imaging unit 121, a delay time distribution image of fluorescent light and a range image may be acquired by optically separating (wavelength separation) and acquiring fluorescent light and reflected light acquired from an object. This can be achieved by providing, for example, in part of a color filter of a color camera such as a Bayer array camera, a filter that cuts light having a wavelength that falls within a fluorescent wavelength band, but that allows near-infrared light to transmit. In this configuration, a delay time for fluorescent light is acquired from a pixel into which light enters through an RGB filter. A delay time for reflected light is further acquired from a pixel into which light enters through a near-infrared filter that blocks visible light. A delay time distribution image of fluorescent light and a range image are acquired based on a delay time for fluorescent light and a delay time for reflected light. A plurality of imaging devices using dichroic mirrors or dichroic prisms may in here be used to configure an imaging unit, instead of using a Bayer array color camera. In this configuration, by only using two types of exposure timing signals as shown in FIG. 3 in exposure in a period corresponding to one frame, a delay time distribution image of fluorescent light and a range image can simultaneously be acquired.

In the present disclosure, two dimensional images have been used to describe images captured and generated by imaging unit 121. However, the present disclosure can apply one dimensional images (line images) and images containing only one pixel to acquire similar effects.

A monochromatic camera has been assumed to describe imaging unit 121 according to this exemplary embodiment. However, capturing images using a color camera or a multi-band camera can acquire similar effects. In this case, in step S202, capturing images with fluorescence spectra in accordance with a number of wavelength bands in the color camera can be achieved. Three types of information, i.e., a delay time distribution image of fluorescent light, a fluorescence spectrum image, and a range image of object 200, can therefore be acquired. A fluorescence spectrum image refers to an image indicative of an intensity in each of a plurality of wavelength bands of fluorescent light radiated by object 200. Since fluorescence spectrum images can be acquired, a plurality of objects 200 would be likely to be distinguished with the fluorescence spectrum images, even when delay times of fluorescent light show equality. In other words, since fluorescence spectrum images can be acquired, a higher identification ability of imaging apparatus 100 can be achieved.

In the present disclosure, after a plurality of types of exposure is performed, images corresponding in number to a number of times of exposure are acquired. However, images may be added and stored in a single memory per exposure, and then an image may be acquired after a plurality of times of exposure.

Figure 12:
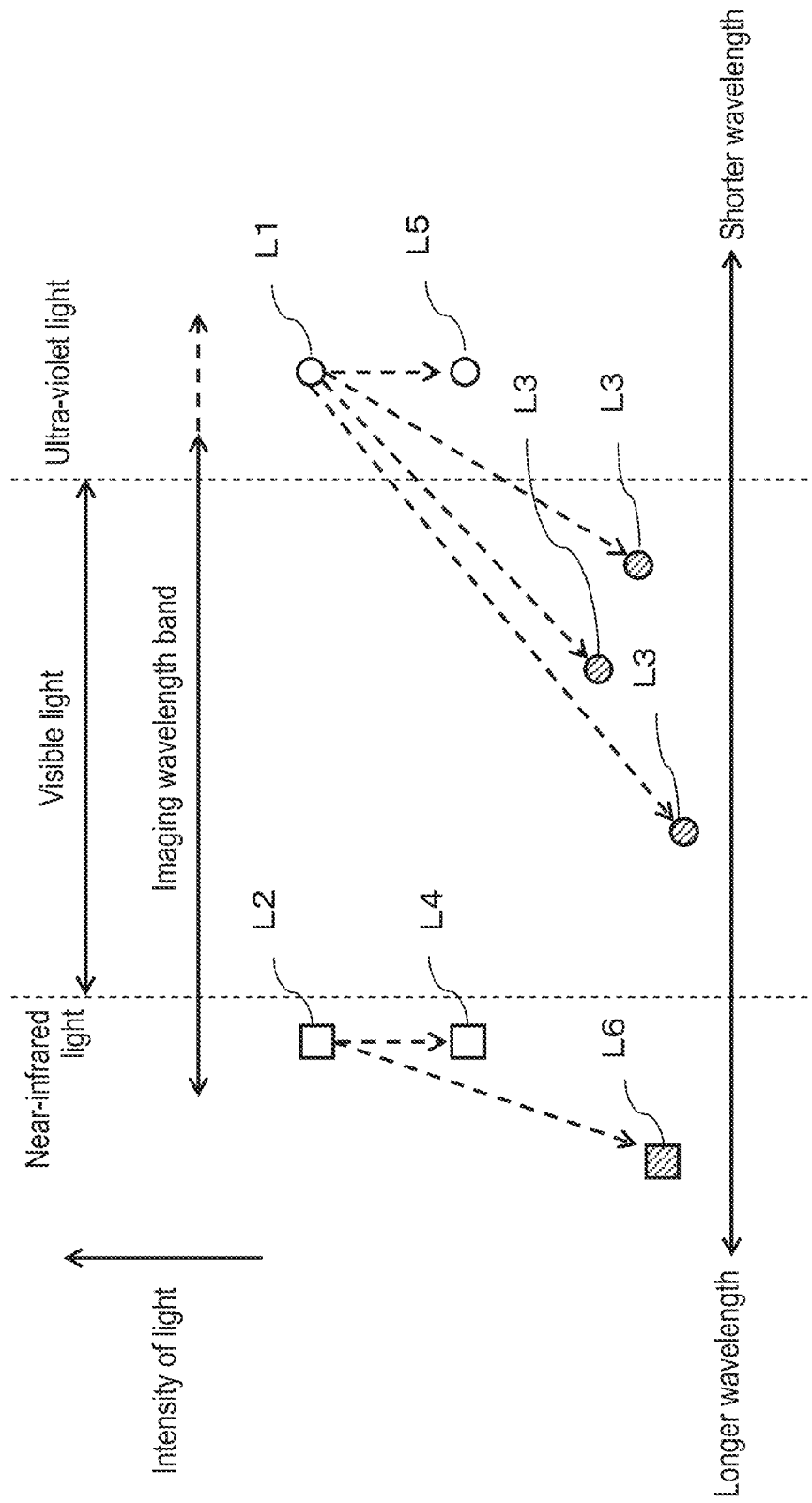
FIG. 12 is a view for describing relations between an imaging wavelength band and wavelengths of excitation light and illumination light.

A relation between wavelengths of excitation light L1 and illumination light L2 and an imaging wavelength band for imaging unit 121 will now be described herein with reference to FIG. 12. In FIG. 12, a horizontal axis shows a wavelength of light. Shorter wavelengths lie on a right side of the horizontal axis, while longer wavelengths lie on a left side. In FIG. 12, a vertical axis shows an intensity of light. Visible light represents a band of wavelengths, light of which can be viewed by human eyes. Imaging wavelength band represents a band of wavelengths, light of which can be captured in images by imaging unit 121.

Upon lighting unit 110 illuminates object 200 with excitation light L1, object 200 radiates fluorescent light L3, as well as emits reflected light L5 caused when object 200 reflects excitation light L1. A wavelength of reflected light L5 and a wavelength of excitation light L1 are identical to each other. Although it may differ depending on a reflection factor of a wavelength of excitation light L1 emitted to object 200, an intensity of reflected light L5 is generally greater than an intensity of fluorescent light L3. When lighting unit 110 illuminates object with illumination light L2, object 200 reflects illumination light L2 and emits reflected light L4. A wavelength of reflected light L4 and a wavelength of illumination light L2 are identical to each other. When object 200 illuminated with illumination light L2 radiates fluorescent light L6, fluorescent light L6 has a wavelength longer than a wavelength of reflected light L4, as well as has an intensity generally weaker than an intensity of reflected light L4.

In the first and second exemplary embodiments of the present disclosure, imaging unit 121 (image acquisition unit) captures an image with light having a wavelength that falls within the imaging wavelength band. The imaging wavelength band represents a band of wavelengths limited by characteristics of an image sensor and a filter used in imaging unit 121. A wavelength of illumination light L2 is set so as to fall within the imaging wavelength band. An advantageous wavelength of excitation light L1 is one that does not fall within the imaging wavelength band, and shorter than wavelengths that fall within the imaging wavelength band. Even when fluorescent light L3 and reflected light L5 are illuminated, imaging unit 121 can therefore capture an image with fluorescent light L3 only. Since an intensity of reflected light L5 is generally greater than an intensity of fluorescent light L3, non-negligible noise would arise in measuring a delay time for fluorescent light L3. Since a wavelength of excitation light L1 is shorter than wavelengths that fall within the imaging wavelength band, imaging unit 121 can further precisely measure a delay time for fluorescent light L3 having a wavelength that falls within the imaging wavelength band.

Imaging unit 121 may in here include a filter for limiting the imaging wavelength band. As shown in a portion rendered with a broken line on the imaging wavelength band in FIG. 12, when an imaging wavelength band includes a wavelength of excitation light L1, reflected light L5 can cause noise, and thus a delay time for fluorescent light L3 would be less likely to precisely be measured. Use of a filter in imaging unit 121 for blocking such a wavelength of excitation light L1 allows imaging unit 121 to further precisely measure a delay time for fluorescent light L3 having a wavelength that falls within the imaging wavelength band.

When a color filter is used in imaging unit 121 for capturing an image, an imaging wavelength band for imaging unit 121 is limited by the color filter. When such a color filter is an RGB filter, imaging unit 121 includes a plurality of imaging wavelength bands respectively corresponding to colors of the RGB filter. Fluorescent light L3 excited by excitation light L1 can have various wavelengths depending on substances configuring object 200. When imaging unit 121 includes a plurality of different imaging wavelength bands, imaging unit 121 would be able to identify a plurality of types of fluorescent light L3 each having a different wavelength. As described above, when imaging unit 121 includes a plurality of imaging wavelength bands, imaging unit 121 may be configured to acquire delay time distribution images of fluorescent light, as well as to acquire fluorescence spectra.

Imaging apparatus 100 according to the present disclosure may advantageously use ultra-violet light as excitation light L1, and further use infrared light as illumination light L2. An advantageous wavelength of illumination light L2 is, in particular, a wavelength of near-infrared light that is difficult to see by human eyes, but that can be detected by an image sensor at relatively higher sensitivity. An advantageous wavelength of illumination light L2 is, specifically, 780 nm or greater. As shown in FIG. 12, illumination light L2, reflected light L4, and fluorescent light L6 to be excited by illumination light L2 can therefore each have a wavelength that does not fall within a visible light band. Capturing images by imaging apparatus 100 can thus be less likely to be seen. Use of ultra-violet light as excitation light L1 can allow excitation light L1 and reflected light L5 to each have a wavelength that does not fall within the visible light band. Since excitation light L1 does not have a wavelength that falls within an imaging wavelength band for imaging unit 121, measuring a delay time using reflected light L5 might be difficult. By using illumination light L2 having a wavelength that differs from a wavelength of excitation light, a delay time for reflected light can be measured even when imaging unit 121 only includes a single imaging wavelength band. In other words, when a wavelength of excitation light L1 does not fall within an imaging wavelength band for imaging unit 121, and a wavelength of illumination light L2 is longer than a wavelength of visible light, excitation light L1 and illumination light L2 can be less likely to be seen when capturing an image.

A wavelength of fluorescent light L3 to be excited by excitation light L1 often falls within a visible light band. However, since imaging unit 121 captures an image with fluorescent light L3 at higher sensitivity, a delay time distribution image of fluorescent light can be acquired even when an intensity of fluorescent light L3 is weaker. In this case, by reducing an illumination intensity of excitation light L1, fluorescent light L3 can be less likely to be seen. Lighting unit 110 illuminates excitation light L1 or illumination light L2 at a predetermined illumination timing, and imaging unit 121 repeats exposure at an exposure timing synchronized with the illumination timing in a predetermined exposure time. An SN ratio can therefore be kept higher, and an image can be captured with fluorescent light L3 at higher sensitivity. Imaging unit 121 may change a predetermined exposure time between when lighting unit 110 illuminates excitation light L1 and when lighting unit 110 illuminates illumination light L2. Higher sensitivity of imaging unit 121 with respect in particular to fluorescent light L3 can therefore be achieved.

Imaging unit 121 may estimate an intensity of fluorescent light L3 radiated from object 200 based on a difference between an image captured by illuminating excitation light L1 for a period equal to or longer than a delay time for fluorescent light L3 and an image captured without illuminating excitation light L1.

Functional components (functional blocks) in an imaging apparatus according to the present disclosure may be implemented as single chips respectively, or a single chip may incorporate some or all of the functional blocks, by means of a semiconductor device such as an integrated circuit (IC) or Large Scale Integration (LSI). A method of implementing integrated circuitry is not limited to LSI, and implementation by means of dedicated circuitry or a general-purpose processor may also be used. A field programmable gate array (FPGA) for which programming is possible after LSI fabrication, or a reconfigurable processor allowing reconfiguration of connections and settings of circuit cells within an LSI, may also be used in implementing integrated circuitry. Further, if a new integrated circuit implementation technology comes out to replace the LSI as a result of the development of semiconductor technology or a derivative other technology, naturally the functional blocks may be integrated using that technology. For example, application of biotechnology is possible.

Further, all of or a part of various processes described above (e.g., procedures shown in FIGS. 2, 8) may be implemented by a hardware product such as an electronic circuit, or may be implemented by using software. Further, software and hardware may be implemented in a mixed manner for processing. It is to be noted that a process using software is implemented in such a way that a processor in an imaging apparatus executes a program stored in a memory. When processing of the above described exemplary embodiments is implemented with software, some or all of the processing may be performed by separate hardware.

Since the above described exemplary embodiments are for exemplifying the technology of the present disclosure, various modifications, replacements, additions, and omissions can be made within the scope of the appended claims or of their equivalents.

The present disclosure is applicable to imaging apparatuses. Specifically, the present disclosure is applicable to robot visions and monitoring cameras.

What is claimed is:

1. An imaging apparatus comprising:
a lighting unit for illuminating an object with an excitation light and an illumination light; and
an image acquisition unit for capturing an image of a fluorescent light radiated from the object which is illuminated by the excitation light, and an image of a reflected light from the object, which reflects the illumination light as the reflected light, and for calculating and acquiring, based on a delay time from when the excitation light reaches the object to when the fluorescent light is radiated, a delay time distribution image of the fluorescent light.

2. The imaging apparatus according to claim 1, wherein the lighting unit illuminates, in each exposure time that is a time having a predetermined length, one of the excitation light and the illumination light at a predetermined illumination timing, and the image acquisition unit captures an image of corresponding one of the fluorescent light and the reflected light at an exposure timing synchronized with the illumination timing.

3. The imaging apparatus according to claim 2, wherein the image acquisition unit changes the exposure time in accordance with light illuminated by the lighting unit.

4. The imaging apparatus according to claim 3, wherein
the image acquisition unit captures an image of a light having a wavelength in an predetermined imaging wavelength band,
a wavelength of the illumination light is in the imaging wavelength band of the image acquisition unit, and
a wavelength of the excitation light is shorter than the imaging wavelength band of the image acquisition unit.

5. The imaging apparatus according to claim 4, wherein the illumination light is near-infrared light, and the excitation light is ultra-violet light.

6. The imaging apparatus according to claim 2, wherein the image acquisition unit captures images of the excitation light at two exposure timings, and images of the reflected light at other two exposure timings.

7. The imaging apparatus according to claim 6, wherein
the image acquisition unit captures an image of a light having a wavelength in an predetermined imaging wavelength band,
wavelength of the illumination light is in the imaging wavelength band of the image acquisition unit, and
wavelength of the excitation light is shorter than the imaging wavelength band of the image acquisition unit.

8. The imaging apparatus according to claim 7, wherein the illumination light is near-infrared light, and the excitation light is ultra-violet light.

9. The imaging apparatus according to claim 2, wherein
the image acquisition unit captures an image of a light having a wavelength in an predetermined imaging wavelength band,
wavelength of the illumination light is in the imaging wavelength band of the image acquisition unit, and
wavelength of the excitation light is shorter than the imaging wavelength band of the image acquisition unit.

10. The imaging apparatus according to claim 9, wherein the illumination light is near-infrared light, and the excitation light is ultra-violet light.

11. The imaging apparatus according to claim 1, wherein
the lighting unit exclusively illuminates the excitation light and the illumination light in each exposure time, having a predetermined length, at respective predetermined illumination timings, and
the image acquisition unit captures an image of the reflected light or the fluorescent light at an exposure timing synchronized with the corresponding illumination timing.

12. The imaging apparatus according to claim 11, wherein the image acquisition unit captures images of the excitation light at two exposure timings, and images of the reflected light at other two exposure timings.

13. The imaging apparatus according to claim 12, wherein
the image acquisition unit captures an image of a light having a wavelength in an predetermined imaging wavelength band,
wavelength of the illumination light is in the imaging wavelength band of the image acquisition unit, and
wavelength of the excitation light is shorter than the imaging wavelength band of the image acquisition unit.

14. The imaging apparatus according to claim 13, wherein the illumination light is near-infrared light, and the excitation light is ultra-violet light.

15. The imaging apparatus according to claim 1, wherein the image acquisition unit
calculates, for each pixel, a time of flight (TOF) of the illumination light based on the captured image of the reflected light,
calculates, for each pixel, a TOF of the excitation light based on the captured image of the fluorescent light, and
acquires the delay time distribution image of the fluorescent light by calculating a time of fluorescence delay, based on the TOF of the illumination light and the TOF of the excitation light, for each pixel.

16. The imaging apparatus according to claim 1, wherein
the image acquisition unit captures an image of a light having a wavelength in an predetermined imaging wavelength band,
wavelength of the illumination light is in the imaging wavelength band of the image acquisition unit, and
wavelength of the excitation light is shorter than the imaging wavelength band of the image acquisition unit.

17. The imaging apparatus according to claim 16, wherein the illumination light is near-infrared light, and the excitation light is ultra-violet light.

18. The imaging apparatus according to claim 1, wherein the image acquisition unit acquires a fluorescence spectrum image by capturing an image of the fluorescent light.

19. An imaging method comprising:
illuminating an object with an excitation light and an illumination light;
capturing an image of a reflected light from the object, which reflects the illumination light as the reflected light, and an image of a fluorescent light radiated by the object which is illuminated by the excitation light; and
acquiring a delay time distribution image of the fluorescent light.

* * * * *